United States Patent [19]

Franke

[11] 4,099,060
[45] Jul. 4, 1978

[54] X-RAY APPARATUS FOR PRODUCING TRANSVERSAL LAYER IMAGES

[75] Inventor: Kurt Franke, Erlangen, Germany

[73] Assignee: Siemens Aktiengesellschaft, Berlin & Munich, Germany

[21] Appl. No.: 782,188

[22] Filed: Mar. 28, 1977

[30] Foreign Application Priority Data

May 4, 1976 [DE] Fed. Rep. of Germany ....... 2619719

[51] Int. Cl.² .................. A61B 6/02; G01N 23/08
[52] U.S. Cl. .................................. 250/445 T; 250/505
[58] Field of Search .................... 250/445 T, 505 T

[56] References Cited

U.S. PATENT DOCUMENTS

| | | | |
|---|---|---|---|
| 3,790,799 | 2/1974 | Stein et al. | 250/505 |
| 3,944,833 | 3/1976 | Hounsfield | 250/445 T |

Primary Examiner—Alfred E. Smith
Assistant Examiner—T. N. Grigsby
Attorney, Agent, or Firm—Hill, Gross, Simpson, Van Santen, Steadman, Chiara & Simpson

[57] ABSTRACT

In an illustrated embodiment linear scanning of a narrow x-ray beam is produced by linear movement of an apertured diaphragm interposed between the x-ray source and the patient receiving space, a measuring arrangement being linearly moved in step with the diaphragm aperture so as to provide a desired number of samples such as one hundred, for each angular position of the components. In the illustrated embodiment a primary diaphragm is interposed between the x-ray source and the linearly movable diaphragm and serves to determine the beam angle in accordance with the scanning range of the measuring arrangement.

2 Claims, 3 Drawing Figures

X-RAY APPARATUS FOR PRODUCING TRANSVERSAL LAYER IMAGES

BACKGROUND OF THE INVENTION

This invention relates to an x-ray apparatus for producing transversal layer images of a photographic subject, including an x-ray source, a diaphragm for condensing the x-rays into a narrow x-ray beam whose cross-sectional spread is equal to the thickness of the layer in a direction perpendicular to the layer and substantially equal to or less than the thickness of the layer in a direction parallel to the layer, and with a measuring arrangement for measuring the intensity of radiation which is impinged upon by the central ray of the x-ray beam, in which, for penetrating the subject from different directions, the x-ray source and the measuring arrangement are arranged together on a rotating frame which is rotatable through equidistant angular steps about a point situated on the central ray of the total radiation emanating from the x-ray tube and in which the measuring arrangement is mounted on the rotating frame on a carriage which is displaceable by a motor perpendicularly of the central ray and the axis of rotation, and further including a cumputer for determining the absorption values of the points of intersection of the radiation in the subject from the intensity of the radiation received by the measuring arrangement.

An x-ray apparatus of this type is described in U.S. Pat. No. 3,778,614. In this known x-ray apparatus, the x-ray tube is arranged on the same carriage as the measuring arrangement so that it is displaceable together with the measuring arrangement perpendicularly of the central ray of the x-ray beam and the axis of rotation. The diaphragm is stationary in relation to the x-ray tube. An x-ray tube is a relatively heavy component so that the mechanics involved in the mounting and displacement of the x-ray tube/measuring arrangement unit are relatively complicated. In addition, guide means are required for the high-tension lead to the x-ray tube to allow linear displacement of the x-ray tube during the scanning operation.

SUMMARY OF THE INVENTION

The object of the present invention is to considerably simplify an x-ray apparatus of the type described above in regard to the mounting and adjustment mechanism for the x-ray tube and the measuring arrangement in relation to the prior art.

According to the invention, this object is achieved by virtue of the fact that the x-ray source is fixedly arranged on the rotating frame, by virtue of the fact that the diaphragm is mounted for displacement parallel to the adjustment path of the measuring arrangement and by virtue of the fact that a motor for displacing the diaphragm is connected to a control device which conrols this motor and also the motor for displacing the measuring arrangement in such a way that, during its displacement, the measuring arrangement is struck by the x-ray beam in each position. In the x-ray apparatus according to the invention, the x-ray tube is not displaced for a linear scanning of the subject under examination. It is merely the measuring arrangement and a relatively lightweight x-ray diaphragm which are displaced. The structure of the x-ray apparatus can be considerably simplified by virtue of the small linearly moved masses in relation to the prior art.

Other objects, features and advantages of the invention will be apparent from the following detailed description taken in connection with the accompanying sheet of drawings.

DETAILED DESCRIPTION

Figure 1:
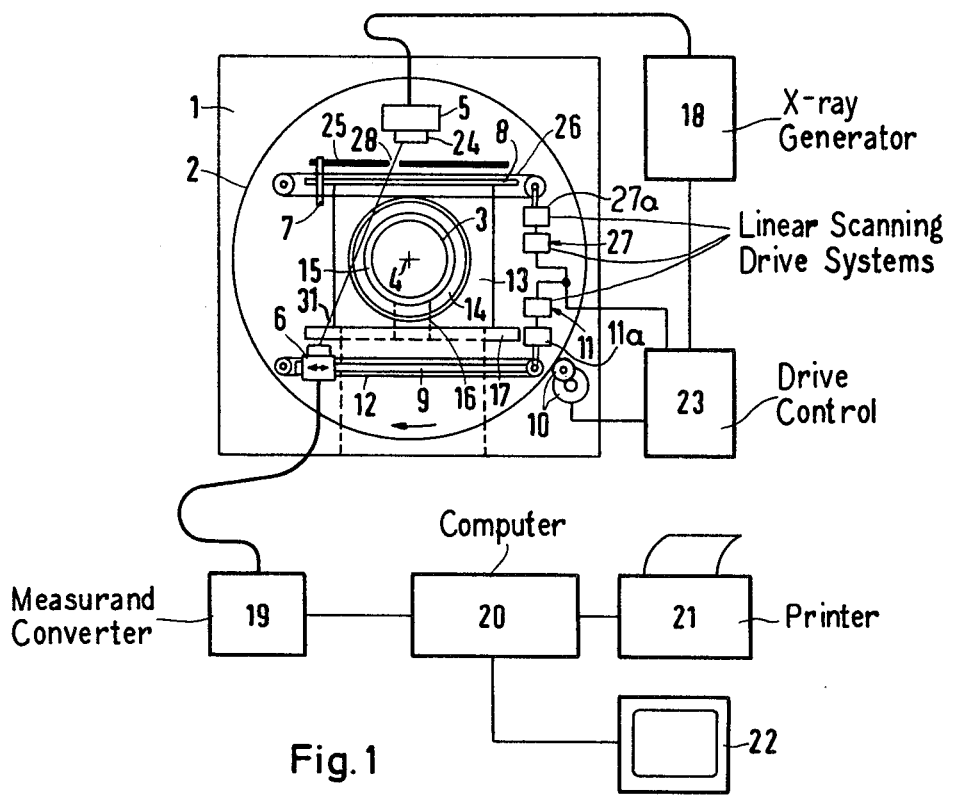
FIG. 1 shows those parts of an x-ray apparatus according to the invention which are of importance to the invention.

In the apparatus shown in FIG. 1, a rotating frame 2 is mounted on a frame member 1 for rotating about an axis 4 which substantially coincides with the longitudinal axis of a subject 3 to be examined. An x-ray tube 5 and a radiation measuring arrangement 6 are mounted on the rotating frame 2. The x-ray tube 5 is fixed to the rotating frame 2, whereas the measuring arrangement 6 is arranged on a rail 9 for linear movement perpendicularly of the central ray of the x-ray tube 5 and the axis of rotation 4. The rotating frame 2 is rotated about the axis 4 by a drive system 10. Another drive system 11 produces the linear scanning movement of the measuring arrangement 6 by means of a cable 12.

A box-shaped (or cuboid) compensating element 13, of a strong plastics material equivalent to body tissue in its density, for example acrylic glass, is also fixedly connected to the rotating frame 2. This compensating body 13 comprises, symmetrically to the axis of rotation 4, a cylindrical recess into which a form-body in the shape of a ring 14, which also consists of a strong plastics material equivalent to body tissue in its density, is slidingly inserted in a form locking manner. A contouring member 15 of an elastic material is attached to the inside of the ring 14. This contouring member 15 can be filled with water by means of a pump (not shown) so that under selectable pressure it will fit firmly against the outside of the photographic subject, which may be the head of a patient, for example. The ring 14 is fixedly connected to a supporting table 17 by means of a bracket or plate 16 so that, despite the rotational movement of the compensating element 13, no torque is applied to the photographic subject 3 resting on the supporting table 17.

The x-ray tube 5 is connected to an x-ray generator 18 which supplies it with constant electrical voltage of selectable magnitude. The radiation receiver 6 is connected via a circuit arrangement or measurand converter 19 to a computer 20 which delivers the data computed by it to a page printer 21 and/or to a data display unit 22 for documentation and/or visual evaluation. The drive system 10 for the circular movement and 11 for the linear movement are connected to a control device 23 which controls the two movements in accordance with a principle of motion to be explained hereinafter.

The x-ray tube 5 is fixedly arranged on the rotating frame 2 and comprises a primary diaphragm 24 which is fixedly arranged in relation to the x-ray tube 5 and which determines the beam (or aperture) angle of the issuing x-rays in accordance with the scanning range of the measuring arrangement 6. Preceding the opening accommodating the photographic subject 3 with respect to the radiation direction is a diaphragm 25 which is displaceable parallel to the path of the measuring arrangement 6 and which is attached to a cable 26 by means of a supporting bar 7. The cable 26 is moved by a drive system 27 including an adjustment motor 27a, the drive system 27 also being connected to the drive control device 23. The diaphragm 25 has a narrow slit 28 which transmits a part of the x-radiation issuing from the x-ray tube 5 which is condensed by the primary diaphragm 24. The x-ray beam allowed through by the slit 28 is used for penetrating the photographic subject 3, and its cross-sectional spread perpendicularly of the layer under examination is equal to the thickness of that layer. Parallel to this layer, the extent of the beam transmitted by primary diaphragm 24 is substantially equal to or less than the thickness of the layer.

After the apparatus has been switched on, the drive control 23 initially actuates the drive system 10 which moves the rotating frame 2 into a starting position offset through 90° relative to the position illustrated. Once this position has been reached, scanning of the object 3 to be examined begins with the drive systems 11 and 27 putting the measuring arrangement 6 and the diaphragm 25 into a linear scanning movement, during which the desired transversal layer of subject 3 is penetrated and scanned with the aid of the x-rays which have been condensed into a narrow beam by means of the diaphragm 25.

Figure 2:
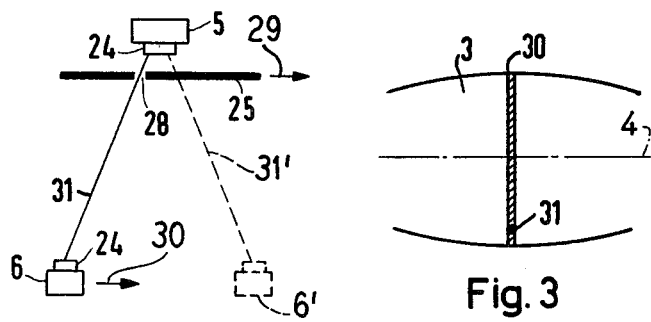
FIG. 2 is a diagrammatic illustration explaining the concept on which the invention is based.

The linear scanning of parts 6, 24 and 25 is shown in FIG. 2. During a scanning movement, the diaphragm 25 and the measuring arrangement 6 are displaced in the direction of the arrows 29 and 30 in such a way that, during its displacement, the measuring arrangement 6 is struck in each position by the x-ray beam which is defined by the aperture 28 of diaphragm 25. The synchronous displacement of the components 6 and 25 is ensured by the control device 23 by way of the drive motors 11a, 27a, FIG. 1. A further position of the beam 31 and measuring arrangement 6 is indicated by dash lines at 31' and 6' in FIG. 2.

The radiation which has penetrated the photographic subject 3 is measured by the measuring arrangement 6 and the measured values are fed by the circuit arrangement 19 into the computer 20 where they are initially stored. During each scanning movement, the output of the measuring arrangement 6 is probed (or sampled) by the circuit arrangement 19 in such a way that, during this movement, approximately 100 individual values are determined and fed into the computer 20. On completion of the first scanning movement, the control device 23 actuates the drive system 10 which rotates the rotating frame 2 through an angle of, for example, 2°. Thereafter, the control device 23 again sets the drive systems 11 and 27 in motion in a direction opposite to the instance described above, so that a second linear scanning movement can take place. On completion of this second scanning movement, the control device 23 switches the drive system 10 on again so that the rotating frame 2 again rotates through an angle of about 2°. Thereafter the control device 23 reactivates the drive systems 11 and 27 so that a third scan can be carried out. This operation is repeated, for example, 90 times. During these scanning movements, the computer 20 computes an image of the penetrated layer on the basis of the measured values fed into it. This image appears either in digital form on the page printer 21 or on the data display unit 22.

Figure 3:
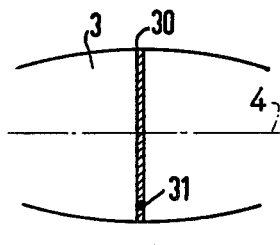
FIG. 3 is a plan view of a patient explaining the dimensions of the x-ray beam issuing from the x-ray tube.

FIG. 3 illustrates a plan view of the photographic subject 3. By way of example, the examined body layer 30 is illustrated. This body layer is scanned by an x-ray beam 31 which is condensed by means of diaphragm 25; namely through its slit 28. In the example, the x-ray beam has an approximately circular cross-section whose diameter is equal to the thickness of layer 30. However, it is also possible within the framework of the invention to limit (or define) the x-ray beam in such a manner that its cross-sectional spread, perpendicular to layer 30, is equal to the thickness of this layer, and that, parallel to layer 30, it is less than the layer thickness.

It will be apparent that many modifications and variations may be effected without departing from the scope of the novel concepts and teachings of the present invention.

I claim as my invention:

1. An x-ray apparatus for producing transversal layer images of a photographic subject, comprising an x-ray source, a diaphragm for condensing the x-rays into a narrow x-ray beam whose cross-sectional spread is equal to the thickness of the layer in a direction perpendicular to the layer and substantially equal to or less than the thickness of the layer in a direction parallel to the layer, comprising a measuring arrangement for measuring the intensity of radiation, in which, for penetrating the subject from different directions, the x-ray source and the measuring arrangement are arranged together on a rotating frame which is rotatable through equidistant angular steps about a point situated on a central ray of the total radiation issuing from the x-ray source and in which the measuring arrangement is mounted on the rotating frame on a carriage which is displaceable by a motor perpendicularly of the central ray and the axis of rotation, and further comprising a computer for determining the absorption values of the points of intersection of the radiation in the subject from the intensity of the radiation received by the measuring arrangement, characterized in that the x-ray source is fixedly arranged on the rotating frame, that the diaphragm is mounted for displacement parallel to the adjustment path of the measuring arrangement and in that a motor for displacing the diaphragm is connected to a control device which controls this motor and also the motor for displacing the measuring arrangement in such a way that, during its displacement, the measuring arrangement is struck by the x-ray beam in each position.

2. An x-ray apparatus as claimed in claim 1, characterized in that the diaphragm is preceded in the direction of radiation by a fixed primary diaphragm which determines the beam angle of the x-rays in accordance with the scanning range of the measuring arrangement.

* * * * *